United States Patent
Bianchetti

[19]

[11] Patent Number: 6,030,210
[45] Date of Patent: Feb. 29, 2000

[54] DENTAL HAND INSTRUMENT WITH INCORPORATED LIGHT SOURCE

[75] Inventor: Fernando Bianchetti, Chiavari, Italy

[73] Assignee: Mectron, S.r.l., Carasco, Italy

[21] Appl. No.: 09/177,833

[22] Filed: Oct. 23, 1998

[30] Foreign Application Priority Data

Nov. 10, 1997 [IT] Italy ............................... MI97A2501

[51] Int. Cl.[7] ............................... A61C 3/00; A61C 1/07
[52] U.S. Cl. ............................................. 433/29; 433/118
[58] Field of Search ............................... 433/29, 118, 119

[56] References Cited

U.S. PATENT DOCUMENTS

| | | | |
|---|---|---|---|
| 3,109,238 | 11/1963 | Marks | 433/29 |
| 4,184,196 | 1/1980 | Moret et al. | 433/29 |
| 4,634,379 | 1/1987 | Mossle et al. | 433/29 |

FOREIGN PATENT DOCUMENTS

| | | | |
|---|---|---|---|
| 3328603 | 2/1985 | Germany | 433/29 |
| 37 06 934 | 9/1988 | Germany . | |
| 3706934 | 9/1988 | Germany | 433/29 |
| 195 13 616 | 10/1995 | Germany . | |

Primary Examiner—John J. Wilson
Attorney, Agent, or Firm—Chernoff, Vilhauer, McClung & Stenzel, LLP

[57] ABSTRACT

A dental hand instrument consisting of a body (1) destined to be coupled at one end with a cover (14) and at the other end with an electrical and hydraulic connector (4); inside said body is positioned a transducer (2) destined to vibrate a workpiece (10) that effects removal of tartar and plaque from the tooth surface, wherein the power supply of the light source of the hand instrument is taken from the power supply of the transducer (2).

7 Claims, 3 Drawing Sheets

DENTAL HAND INSTRUMENT WITH INCORPORATED LIGHT SOURCE

BACKGROUND AND SUMMARY OF THE INVENTION

The present invention refers to a dental hand instrument with incorporated light source.

The invention refers in particular to a surgical instrument employed by dentists for scaling and removing tartar and plaque from the tooth surface, commonly called a hand instrument, provided with a light source for illuminating the working area in the patient's oral cavity.

The hand instrument is provided with a transducer that serves to vibrate a hooked instrument called a workpiece that provides for removal of tartar from the tooth surface. Said workpiece has a through hole wherefrom a cleaning fluid which aids the cleaning operation on the oral cavity can be discharged.

Although dental surgeries are well lit it can happen that the dentist casts a shadow over the oral cavity with his body, his hand or the instrument itself as he works. This has led to the need to direct a beam of light around the workpiece of the hand instrument.

Different types of hand instruments are currently known to the art. All the known hand instruments use a separate power supply from that of the transducer of the hand instrument for their light sources.

In fact, because of the need to have a light source that gives a high luminous energy the hand instruments according to the known art use iodine filament lamps.

According to current health regulations, hand instruments must be able to be autoclaved, that is they must be periodically washed and sterilized in an autoclave at high temperatures. Said iodine filament lamps cannot withstand these extremely high temperatures and therefore they must be placed outside the hand instrument, in special separate connectors. Moreover, the possibility of inserting said lamps in the body of the hand instrument has not been considered thus far, both because of their large size which would considerably compromise the manageability of the instrument and because the life of said lamps is very short and therefore they must be positioned in a housing that is readily accessible to the user to facilitate replacement.

Said hand instruments according to the prior art have various drawbacks.

In fact, the use of a separate power supply and external connectors for the light source results in a very bulky instrument with poor versatility because special circuitry must be used for the lamps.

The white light coming from the filament lamps is used only for illumination and in addition presents a further problem. In fact during the cleaning operation said light, entering into contact with the splashes of cleaning fluid coming from the hole in the workpiece, causes misting which prevents clear visibility.

The object of the invention is to eliminate these drawbacks at the same time providing a hand instrument that is simple to make.

This object is reached according to the invention with the characteristics listed in claim 1.

Preferred embodiments of the invention emerge from the dependent claims.

In the hand instrument according to the invention the power supply for the light sources is provided by the same power supply as for the transducer of the hand instrument. With this expedient even high-efficiency LEDs and laser diodes can be used as light sources. In fact LEDs have a good resistance to high temperatures and can withstand the autoclave sterilization process without being damaged.

LEDs also have a very long life compared to lamps and do not need to be replaced for long periods, therefore they can be made integral with the body of the hand instrument and the same power supply as for the hand instrument transducer can be used for the LEDS. For the aforementioned reasons a single connector can be used that is coupled with a mating connector connected to the external supply cable. In this manner there is a considerable reduction in the size of the instrument, a saving in circuitry because further connectors are not used and better versatility since said configuration can also be used for other types of compatible instruments.

Moreover, high-efficiency LEDs which transmit a blue light for diagnostic purposes can be used advantageously.

To overcome the problem of illumination of the oral cavity a mixture of light beams of a plurality of LEDs that emit at different frequencies can be employed in order to be able, through the known RGB combination method, to obtain a white light that allows optimal visibility of the oral cavity without the problem of misting.

Further characteristics of the invention will be made clearer by the detailed description that follows, referring to a purely exemplary and therefore non-limiting embodiment thereof, illustrated in the appended drawings.

DETAILED DESCRIPTION OF THE PREFERRED EMBODIMENTS

The hand instrument according to the invention will now be described with the aid of the figures.

Figure 1:
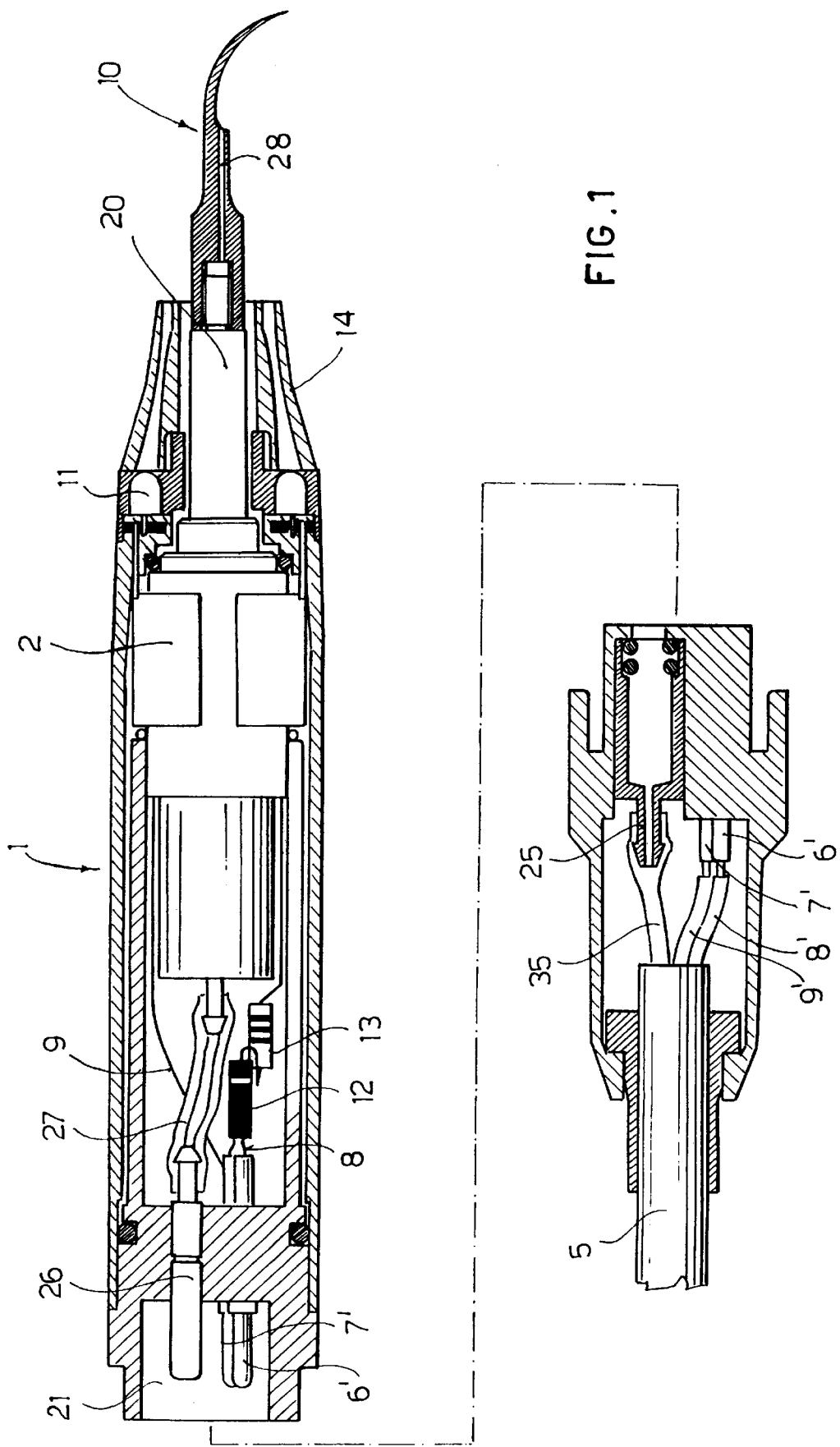
FIG. 1 shows an axial section of the hand instrument according to the invention with the connector element thereof.
Figure 2:
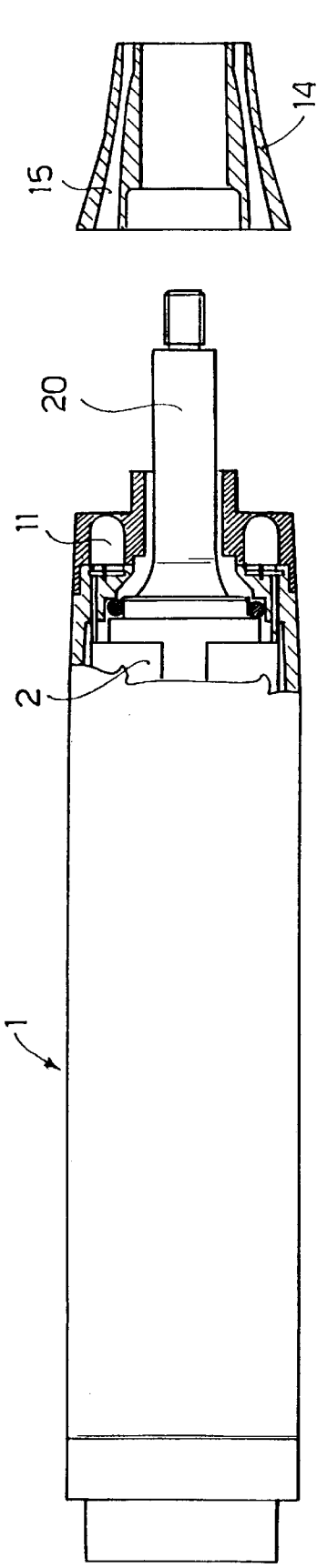
FIG. 2 shows a partial section of the hand instrument according to the invention with the stopper element removed.

In FIG. 1 a hand instrument consisting of a hollow cylindrical-shaped body 1 can be seen. Inside said body a transducer 2 is positioned. Said transducer consists of a piezoelectric ceramic resonator that is powered in alternating current and acts as a concentrator for sound waves which are transmitted, through a metallic cylindrical arm 20, to a hooked workpiece 10 which by entering into vibration carries out removal of the tartar and plaque from the patient's teeth. A through hole 28 is formed in said workpiece for discharge of the cleaning liquid.

At the end of the body 1 of the hand instrument where the workpiece 10 is connected housings are formed wherein the LEDs 11 are positioned. A hollow truncated conical shaped cover 14 which partially covers the cylindrical arm 20 is coupled to said end allowing the workpiece 10 to protrude. Through cavities are formed in the body of said cover 14 wherein optical fibres or light guides 15 are positioned so that there is a perfect coupling with the light emitting surface of the LEDs 11.

At the other end of the body of the hand instrument is an electrical and hydraulic connector 21 destined to engage with a matching electrical and hydraulic connector 4 that carries an outer sheath 5. A cleaning fluid feed tube 35, an electrical power supply cable 8' and a grounding cable 9' are passed inside said sheath.

Inside the complementary connector element 4 the cleaning fluid feed tube 35 is connected to a hydraulic coupling 25, the electrical power supply cable 8' is connected to an electrical power supply contact 6 and the grounding cable 9' is connected to a contact to earth 7. The hydraulic coupling 25 engages with a hydraulic connector 26 formed in the connector element 21. A tube element 27 is connected to the hydraulic connector 26. Said tube element 27 is used to convey the cleaning fluid inside the body 1 of the hand instrument in such a manner that said fluid can leave the hole 28 formed in the workpiece 10 at an adequate pressure.

The electrical contacts 6, 7 are destined to engage with respective matching contacts 6', 7' formed in the connector 21 integral with the body 1 of the hand instrument. Said contacts 6', 7' are connected to a power supply cable 8 and a grounding cable 9, respectively. The power supply cable 8 and the grounding cable 9 are connected to the transducer 2 so as to provide the necessary alternating-voltage power supply.

Figure 5:
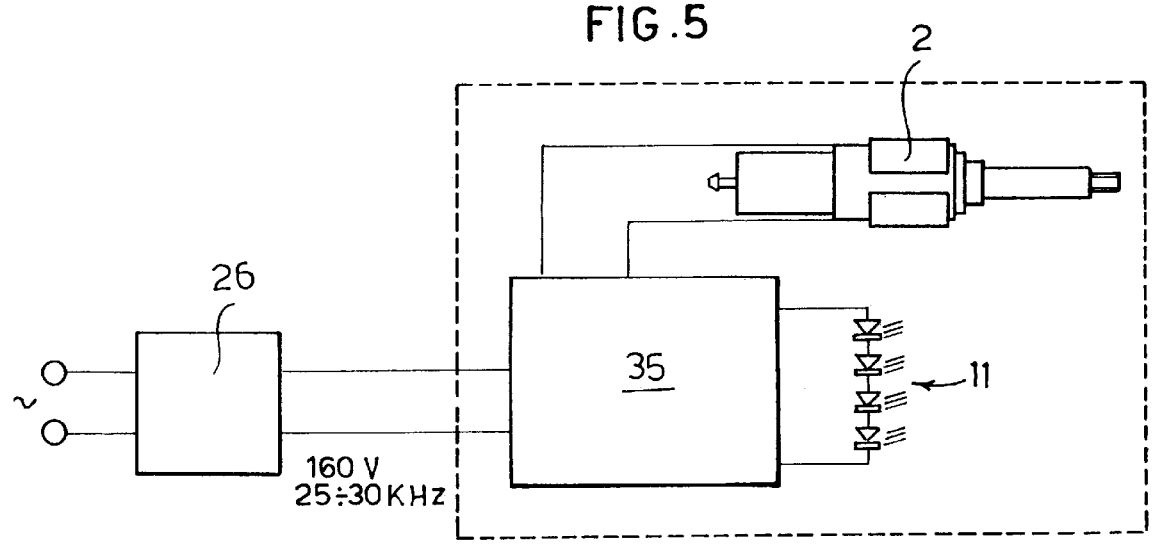
FIG. 5 shows a general wiring diagram of the LED connection circuit.

Polarization of the LEDs 11 can be obtained, for example, using the circuit diagram in FIG. 5. In said diagram the LEDs are connected in series and are polarized through an electronic circuit 35 connected to the power supply cable 8. Said power supply cable 8 comes from a transformer 26 that transforms the line voltage into an alternating 160 Volt r.m.s sinusoidal voltage at a frequency oscillating between 25 KHz and 30 KHz, necessary for the power supply to the piezoelectric ceramic resonator. The electronic circuit can be inductive or capacitive or of another type.

Figure 6:
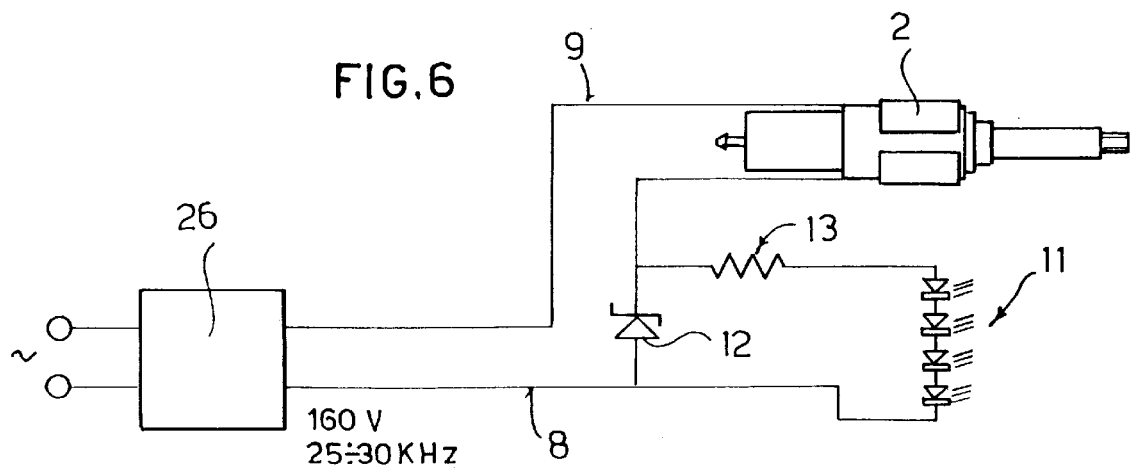
FIG. 6 shows a particular embodiment of the LED connection circuit.

In particular in FIG. 6 a preferred embodiment of the LED polarization circuit is shown. In this case polarization of the LEDs is obtained by means of a Zener 12 diode in series with a resistance 13 connected to the power supply cable 8.

Figure 3:
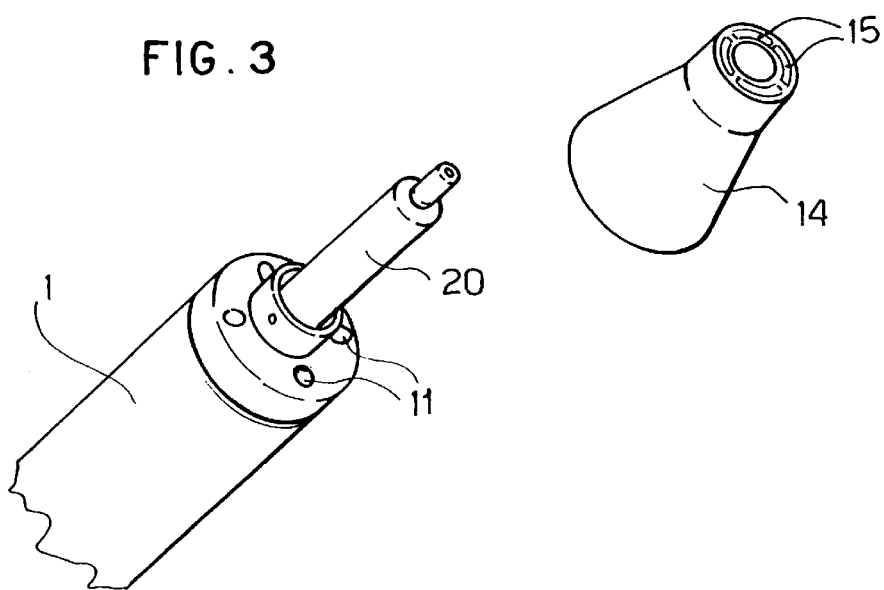
FIG. 3 shows an axonometric view of one end of the hand instrument according to the invention showing a possible type of housing for optical fibres or light guides.

In FIGS. 1 and 3 a preferred embodiment of the invention is presented wherein four LEDs 11 are positioned in their own housings spaced from each other by an angle of about 90° on the circumference of the end of the body 1 of the hand instrument.

Four through cavities are formed in the cover 14 for four optical fibres or light guides 15 destined to be coupled with four LEDs 11.

Figure 4:
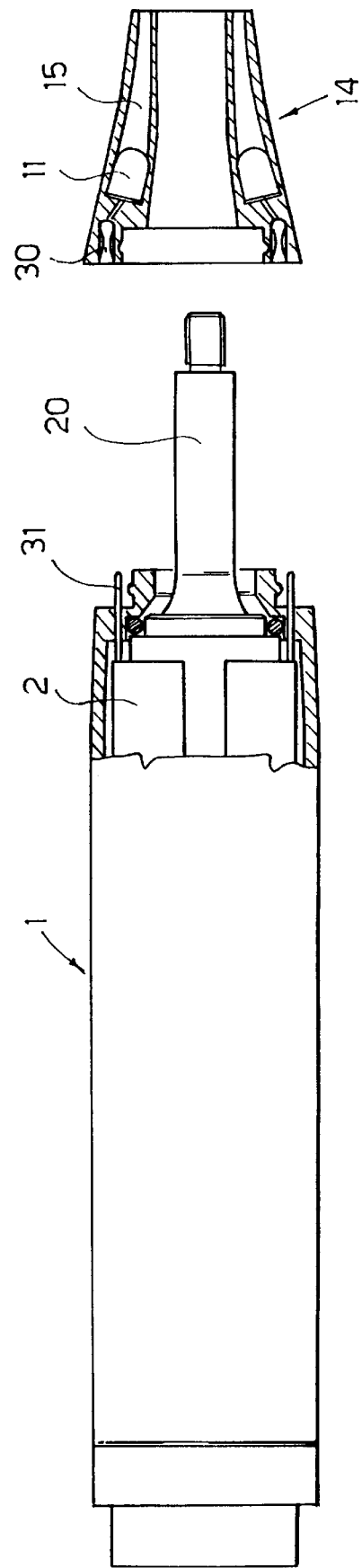
FIG. 4 shows an exploded partial section of a further embodiment of the hand instrument according to the invention.

FIG. 4 shows a further embodiment of the hand instrument according to the invention wherein some LEDs are positioned in a housing formed in the body of the cover 14 and coupled directly with the respective optical fibres or light guides 15. This solution must provide electrical connectors 30 connected to the LEDs 11 that engage with the respective mating electrical connectors 31 connected with a diode polarization circuit inside the body 1 of the hand instrument and supplied by the same power supply as the transducer 2 of the hand instrument.

I claim:

1. A dental hand instrument comprising: a body (1) inside which is positioned a transducer (2) used to vibrate a workpiece (10) in particular serving to remove tartar and plague from the tooth surface, a cover (14) coupled to said body, a light source to illuminate the work area, and an external connector (4) to provide the electrical power supply to the transducer (2) characterized in that said light source emits blue light and in that the power supply to said light source is taken partly or entirely from the power supply to the transducer (2) of the hand instrument.

2. A dental hand instrument according to claim 1, characterized in that said light source consists of a LED (11).

3. A dental hand instrument according to either of claims 1 or 2 characterized in that optical fibres or light guides (15) focus the light emission coming from said light source.

4. A dental hand instrument according to claim 3, characterized in that said optical fibres or light guides (15) are housed in through cavities formed in the cover (14) of the hand instrument.

5. A dental hand instrument according to claim 2, characterized in that it includes a plurality of said LEDs (11) and that said LEDS (11) are connected in series and are polarized through an electronic circuit (35) supplied in sinusoidal alternating voltage at 160 Volts r.m.s. and frequency oscillating from 25 KHz to 30 KHz.

6. A dental hand instrument according to claim 5, characterized in that said electronic circuit (35) is of the capacitive or inductive type.

7. A dental hand instrument according to claim 5, characterized in that said electronic circuit (35) comprises a Zener diode (12) and a resistance (13) in series.

* * * * *